United States Patent
Claiborne, III et al.

(10) Patent No.: US 9,011,525 B2
(45) Date of Patent: Apr. 21, 2015

(54) CATHETER DELIVERABLE ARTIFICIAL MULTI-LEAFLET HEART VALVE PROSTHESIS AND INTRAVASCULAR DELIVERY SYSTEM FOR A CATHETER DELIVERABLE HEART VALVE PROSTHESIS

(75) Inventors: Thomas E. Claiborne, III, Bayport, NY (US); Richard T. Schoephoerster, El Paso, TX (US); Siobhain L. Gallocher, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 470 days.

(21) Appl. No.: 12/864,166

(22) PCT Filed: Feb. 25, 2009

(86) PCT No.: PCT/US2009/035121
§ 371 (c)(1),
(2), (4) Date: Oct. 28, 2010

(87) PCT Pub. No.: WO2009/111241
PCT Pub. Date: Sep. 11, 2009

(65) Prior Publication Data
US 2011/0295361 A1    Dec. 1, 2011

Related U.S. Application Data

(60) Provisional application No. 61/032,636, filed on Feb. 29, 2008.

(51) Int. Cl.
*A61F 2/24* (2006.01)
*A61F 2/95* (2013.01)

(52) U.S. Cl.
CPC ............. *A61F 2/2412* (2013.01); *A61F 2/2418* (2013.01); *A61F 2/2436* (2013.01);
(Continued)

(58) Field of Classification Search
USPC ................................ 623/2.15, 2.19
See application file for complete search history.

(56) References Cited

U.S. PATENT DOCUMENTS 4,167,045 A    9/1979    Sawyer
4,477,930 A *  10/1984   Totten et al. ............. 623/2.15
(Continued)

FOREIGN PATENT DOCUMENTS

EP    1 690 515 A1    8/2006
JP    3489643 A       3/1997
(Continued)

OTHER PUBLICATIONS

Supplementary European Search Report for Application No. 09717374.4 dated Aug. 2, 2011.
(Continued)

*Primary Examiner* — Jacqueline Woznicki
(74) *Attorney, Agent, or Firm* — Marshall, Gerstein & Borun LLP

(57) ABSTRACT

A heart valve prosthesis includes a collapsible stent and a one-piece multi-leaflet valve. The stent includes at least one length of wire having a series of turns forming a spring-like stent. The one-piece multi-leaflet valve is attached to the stent and includes a cylinder of polyester material secured thereto at three points. The stent is collapsible in a radial direction between a contracted state and an expanded state. The contracted state has a radial dimension smaller than a radial dimension of the expanded state. The stent is spring biased toward the expanded state such that it occupies an active state when implanted into a heart. The active state has a radial dimension that is between the radial dimension of the contracted state and the radial dimension of the expanded state such that a radial load generated by the bias of the collapsible stent is sufficient to retain the heart valve prosthesis in the heart.

11 Claims, 6 Drawing Sheets

(52) U.S. Cl.
    CPC . *A61F2002/9522* (2013.01); *A61F 2220/0075* (2013.01); *A61F 2230/0017* (2013.01); *A61F 2230/0023* (2013.01)

(56) References Cited

U.S. PATENT DOCUMENTS

| | | | |
|---|---|---|---|
| 4,687,483 A | | 8/1987 | Fisher et al. |
| 7,261,732 B2 * | | 8/2007 | Justino ............... 623/1.24 |
| 2001/0007956 A1 * | | 7/2001 | Letac et al. ............ 623/2.11 |
| 2001/0010017 A1 * | | 7/2001 | Letac et al. ............ 623/2.11 |
| 2002/0133226 A1 * | | 9/2002 | Marquez et al. ......... 623/2.11 |
| 2003/0209835 A1 | | 11/2003 | Chun et al. |
| 2005/0049682 A1 * | | 3/2005 | Leanna et al. .......... 623/1.15 |
| 2006/0259136 A1 | | 11/2006 | Nguyen et al. |
| 2009/0082857 A1 * | | 3/2009 | Lashinski et al. ....... 623/2.18 |
| 2011/0137397 A1 * | | 6/2011 | Chau et al. ............ 623/1.11 |
| 2011/0319988 A1 * | | 12/2011 | Schankereli et al. ..... 623/2.11 |
| 2012/0179244 A1 * | | 7/2012 | Schankereli et al. ..... 623/2.11 |
| 2012/0323316 A1 * | | 12/2012 | Chau et al. ............ 623/2.18 |
| 2014/0222142 A1 * | | 8/2014 | Kovalsky et al. ........ 623/2.17 |

FOREIGN PATENT DOCUMENTS

| | | |
|---|---|---|
| WO | WO-01/41679 A1 | 6/2001 |
| WO | WO-03/047468 A1 | 6/2003 |

OTHER PUBLICATIONS

Communication Relating to the Results of the Partial International Search for PCT/US2009/035121, mailed Oct. 15, 2009.

International Search Report for PCT/US2009/035121, mailed Dec. 30, 2009.

Written Opinion for PCT/US2009/035121, mailed Dec. 30, 2009.

* cited by examiner

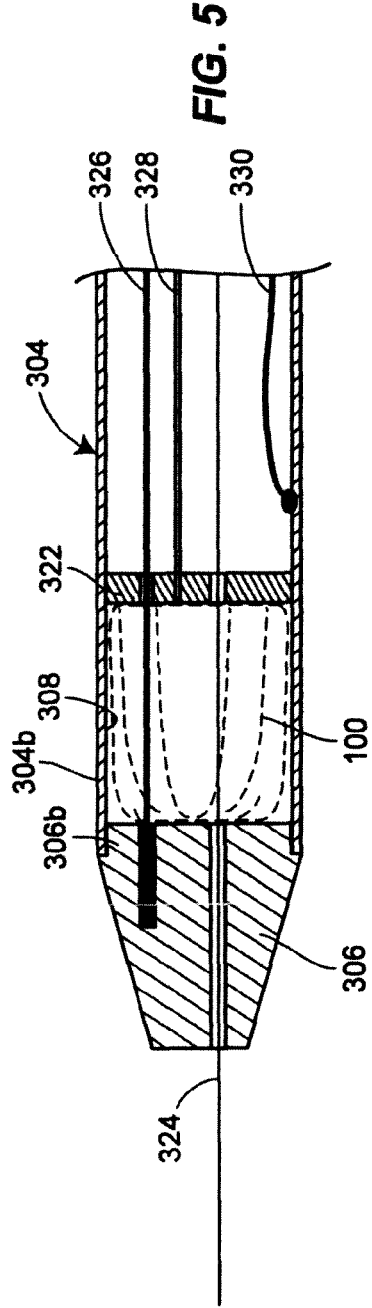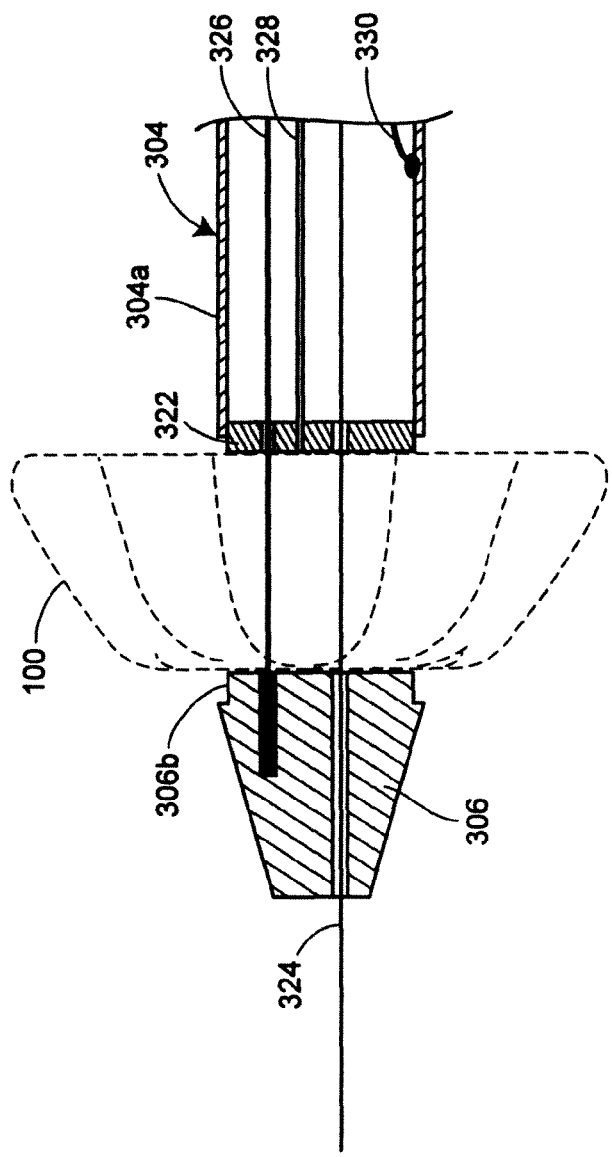

CATHETER DELIVERABLE ARTIFICIAL MULTI-LEAFLET HEART VALVE PROSTHESIS AND INTRAVASCULAR DELIVERY SYSTEM FOR A CATHETER DELIVERABLE HEART VALVE PROSTHESIS

RELATED APPLICATIONS

The priority benefit of U.S. Provisional Patent Application No. 61/032,636, filed Feb. 29, 2008 is hereby claimed and the entire contents thereof are incorporated herein by reference.

FIELD OF THE DISCLOSURE

The present disclosure is generally directed to an artificial heart valve and, more particularly, to a catheter deliverable artificial heart valve and delivery system therefor.

BACKGROUND

The heart is the organ responsible for keeping blood circulating through the body. This task would not be possible if it was not for the action of valves. Four heart valves are key components that facilitate blood circulation in a single direction, and that the contraction force exerted by the heart is effectively transformed into blood flow.

Each time the heart contracts or relaxes, two of the four valves close and the other two open. There are two states of the heart: relaxed or contracted. Depending on the state of the heart, a heart valve has two specific functions: either to open smoothly without interfering blood flow or to close sharply to impede the flow in the opposite direction.

The anatomy of the heart allows it to simultaneously maintain the flow of the two major blood circuits in the body: pulmonary circulation and systemic circulation, which also includes the coronary circulation. This simultaneous action of keeping blood flowing through both circuits requires that the heart valves work in pairs, namely, the tricuspid and the pulmonary valve work together to direct the flow toward the lungs, and the mitral and aortic valves direct the flow toward the rest of the body including the heart.

From the two circulations, the systemic circulation is the one that demands most of the energy of the heart because it operates under higher pressures and greater flow resistance. Consequently, the left heart is more susceptible to valve disorders. This condition makes the aortic and mitral valves primary subjects of research.

According to the American Heart Association it is estimated that around 19,700 people in the United States die every year from heart valve disease, and another 42,000 die from different causes aggravated by valvular problems. During 1996, 79,000 heart valve replacements were carried out in the United States, a quantity that was reported to increase by 5,000 more replacements by 1997. Although improvement has been evident in this area of medical treatments, still a mortality rate between 30% and 55% exists in patients with valvular prostheses during the first 10 years after surgery.

The aortic valve, representing almost 60% of the valve replacement cases, is located at the beginning of the systemic circulation and right next to the coronary ostia. Once the aortic valve closes the oxygenated blood flows into the heart through the right and left coronary arteries.

The mitral valve, located between the left atrium and the left ventricle offers a different set of conditions. Although the mitral valve is not surrounded by any arterial entrances, it is located in a zone with greater access difficulties, and its anatomical structure contains a set of "leaflet tensors" called chordae tendinae.

The human application of prosthetic heart valves goes back to 1960 when, for the first time, a human aortic valve was replaced. Since then, the use of valvular implants has been enhanced with new materials and new designs.

The first mechanical valves used a caged-ball mechanism to control blood flow. Pressure gradients across the occluder-ball produced its movement to close or open the flow area. Even though this design performed the function of a valve, there were several problems associated with it: The ball geometry and the closing impact of the ball against the cage ring were both causes of large downstream turbulence and hemolysis. In addition to blood damage, obstruction to myocardial contraction and thrombogenic materials were also problems.

Several designs having new materials including disks or leaflets instead of balls, improved the hemodynamic performance and durability of the implants, but two critical aspects remain pending for better solutions: 1) the highly invasive surgery required to implant the prosthesis, and 2) the thrombogenic effect of the implant's materials.

Typically, mechanical heart valve prostheses are made from pyrolytic carbon or other prosthetic materials that require rigorous anticoagulant therapy because the risk of coagulation is higher over the surface of the prosthesis. The thrombogenic aspect has drawn the attention of many biomedical institutions towards the creation and study of more biocompatible materials.

Currently, prosthetic heart valve technology includes several designs with disks or leaflets integrated into a rigid stent. This rigid stent is generally surrounded by a sewing cuff which allows the surgeon to suture the interface between the cuff and the tissue. This procedure, however, is highly invasive and its materials generally have a negative thrombogenic effect.

Prosthetic heart valves with rigid stents require open heart surgery for implantation. During the implantation procedure the patient is maintained alive by a heart-lung machine while the surgeon sutures the device into the heart. Due to the highly invasive nature of this procedure, not all individuals suffering from heart valve disease are considered proper candidates.

In those cases where a heart valve replacement has been performed, the risk of coagulation of blood becomes higher over the surface of the prosthesis. Mechanical heart valve prostheses made from pyrolytic carbon or other prosthetic metals require rigorous anticoagulant therapy. Other prosthetic valves use animal tissues, with which the thrombogenic effect is not as severe as for other materials, but durability is noticeably lower. Specifically, prosthetic valves constructed using animal tissue are prone to hardening as a result of being rejected by the body. Such hardening and rejection can ultimately lead to less than optimal performance.

SUMMARY

A heart valve prosthesis includes a collapsible stent and a one-piece multi-leaflet valve. The stent includes at least one length of wire having a series of turns forming a spring-like stent. The one-piece multi-leaflet valve is attached to the stent and includes a cylinder of polyester material secured thereto at three points. The stent is collapsible in a radial direction between an expanded state and a contracted state. The contracted state has a radial dimension smaller than a radial dimension of the expanded state. The stent is spring biased toward the expanded state such that it occupies an active state when implanted into a heart. The active state has a radial dimension that is between the radial dimension of the contracted state and the radial dimension of the expanded state such that a radial load generated by the bias of the collapsible stent is sufficient to retain the heart valve prosthesis in the heart.

In one embodiment, the one-piece multi-leaflet valve further comprises a cylindrical cuff wrapped around an end of the collapsible stent. The cylindrical cuff is for preventing regurgitation during use of the valve.

In one embodiment, the multi-leaflet valve further comprises a polymer coating the polyester material.

Another embodiment further includes surgical sutures connecting the one-piece multi-leaflet valve to the collapsible stent.

In one embodiment, the collapsible stent includes first and second lengths of wire, each of the first and second lengths of wire occupying a sinusoidal pattern.

In one embodiment, the first and second lengths of sinusoidal wires are disposed adjacent to each other and in opposite phase to provide structural integrity to the collapsible stent.

In one embodiment, the collapsible stent further includes a third length of wire occupying a pattern of alternating bows and attached to the first and second lengths of wires at a location axially offset therefrom. The third length of wire serves to bias the collapsible stent into the expanded state.

In one embodiment, the collapsible stent is constructed of a shape memory nickel titanium alloy.

In one embodiment, the collapsible stent occupies a generally tapered cylindrical shape at least when in the expanded state.

In one embodiment, the multi-leaflet valve includes a trileaflet valve.

Another aspect of the present disclosure includes a system for intravascular delivery of a heart valve prosthesis. The system includes a handle, a flexible elongated sheath, a cavity defined by the sheath, and a tapered tip. The flexible elongated sheath extends from the handle. The cavity is defined by an end of the elongated sheath that is disposed opposite the handle. The cavity is adapted to contain a heart valve prosthesis during intravascular delivery of the heart valve prosthesis. The tapered tip is coupled to the end of the elongated sheath adjacent to the cavity. The tapered tip is adapted to guide the elongated sheath during intravascular delivery of the heart valve prosthesis. The tapered tip and the elongated sheath are separable such that the heart valve prosthesis can be released from the cavity in the elongated sheath upon proper positioning of the heart valve prosthesis.

In one embodiment, the elongated sheath has an inner diameter of less than or equal to 7 mm and an outer diameter of less than or equal to 8 mm.

One embodiment further includes a string connected to the elongated sheath at a location adjacent the cavity and extending through the sheath to the handle. So configured, a user can pull the string to bend the elongated sheath to facilitate navigation of the elongated sheath during intravascular delivery of the heart valve prosthesis.

One embodiment further includes a stop plug disposed in the elongated sheath adjacent the cavity. The stop plug prevents the heart valve prosthesis from traveling into the elongated sheath beyond the cavity.

In one embodiment, the elongated sheath is movably mounted to the handle such that movement of the sheath toward the handle separates the elongated sheath and the tapered tip.

Another aspect of the present disclosure includes a device for loading a collapsible heart valve prosthesis into a flexible elongated sheath of an intravascular heart valve delivery system. The device includes a handle, a pin, and a loop of material. The pin is rotatably mounted to the handle. The loop of material has a first end fixed to the handle and a second end fixed to the pin. The loop of material is adapted to receive a collapsible heart valve prosthesis in an expanded state. The pin is rotatable relative to the handle to roll the loop of material onto the pin, thereby applying a radial force to collapse the heart valve prosthesis from the expanded state to a contracted state. A radial dimension of the collapsible heart valve prosthesis in the contracted state is less than a radial dimension of the collapsible heart valve prosthesis in the expanded state such that the collapsible heart valve prosthesis in the contracted state can be loaded into the flexible elongated sheath of the intravascular heart valve delivery system.

In one embodiment, the pin includes a slot formed therein that receives the first end of the loop of material.

BRIEF DESCRIPTION OF THE DRAWINGS

Objects, features, and advantages of the present invention will become apparent upon reading the following description in conjunction with the drawing figures, in which:

FIGS. 5 and 6 are detailed views of the system for intravascular delivery of a collapsible heart valve prosthesis of the present disclosure, illustrating its use and taken from circle V, VI of FIG. 4.

DETAILED DESCRIPTION OF THE DISCLOSURE

Figure 1:
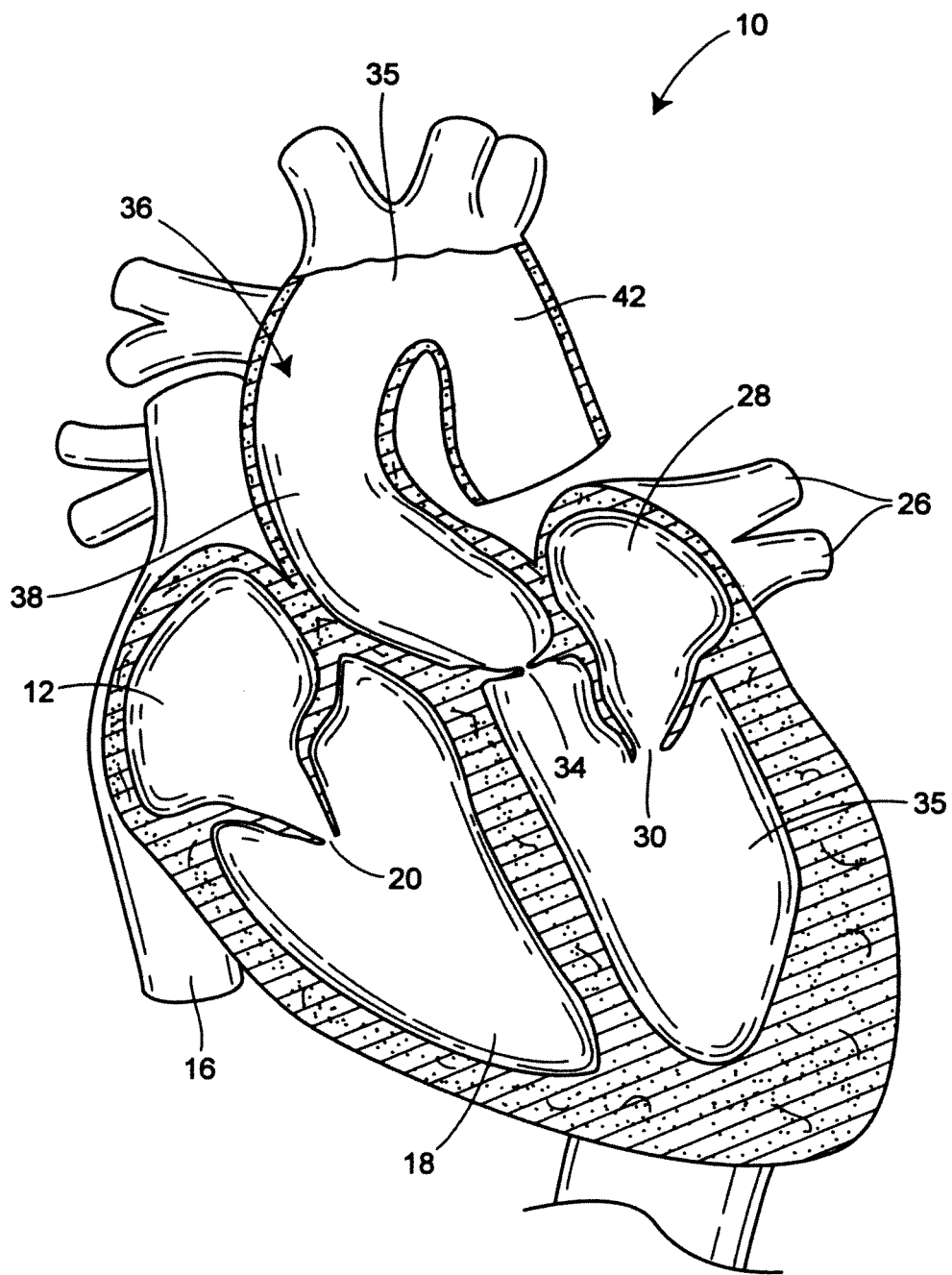
FIG. 1 is a cross-sectional representation of a heart.

FIG. 1 is a schematic cross-sectional illustration of the anatomical structure and major blood vessels of a human heart 10. Deoxygenated blood is delivered to the right atrium 12 of the heart 10 by the superior and inferior vena cava 14, 16. Blood in the right atrium 12 is allowed to pass into the right ventricle 18 through the tricuspid valve 20. Once in the right ventricle 18, the heart 10 delivers this blood through the pulmonary valve to the pulmonary arteries and to the lungs for a gaseous exchange of oxygen. The circulatory pressures carry this blood back to the heart via the pulmonary veins 26 and into the left atrium 28. Filling of the left atrium 28 occurs as the mitral valve 30 opens to allow blood to be drawn into the left ventricle 32 for expulsion through the aortic valve 34 and on to the body extremities through the aorta 36. The aorta 36 comprises (i) an ascending aorta 38, which arises from the left ventricle 32 of the heart 10, (ii) an aortic arch 10, which arches from the ascending aorta 38 and (iii) a descending aorta 42, which descends from the aortic arch 35 towards the abdominal aorta (not shown). When the heart 10 fails to continuously produce normal flow and pressures, a disease commonly referred to as heart failure occurs.

One cause of heart failure is failure or malfunction of one or more of the valves of the heart 10. For example, the aortic valve 34 can malfunction for several reasons. The aortic valve 34 may be abnormal from birth (e.g., bicuspid, calcification, congenital aortic valve disease), or it could become diseased with age (e.g., acquired aortic valve disease). In such situations, it can be desirable to replace the abnormal or diseased valve 34.

Figure 2:
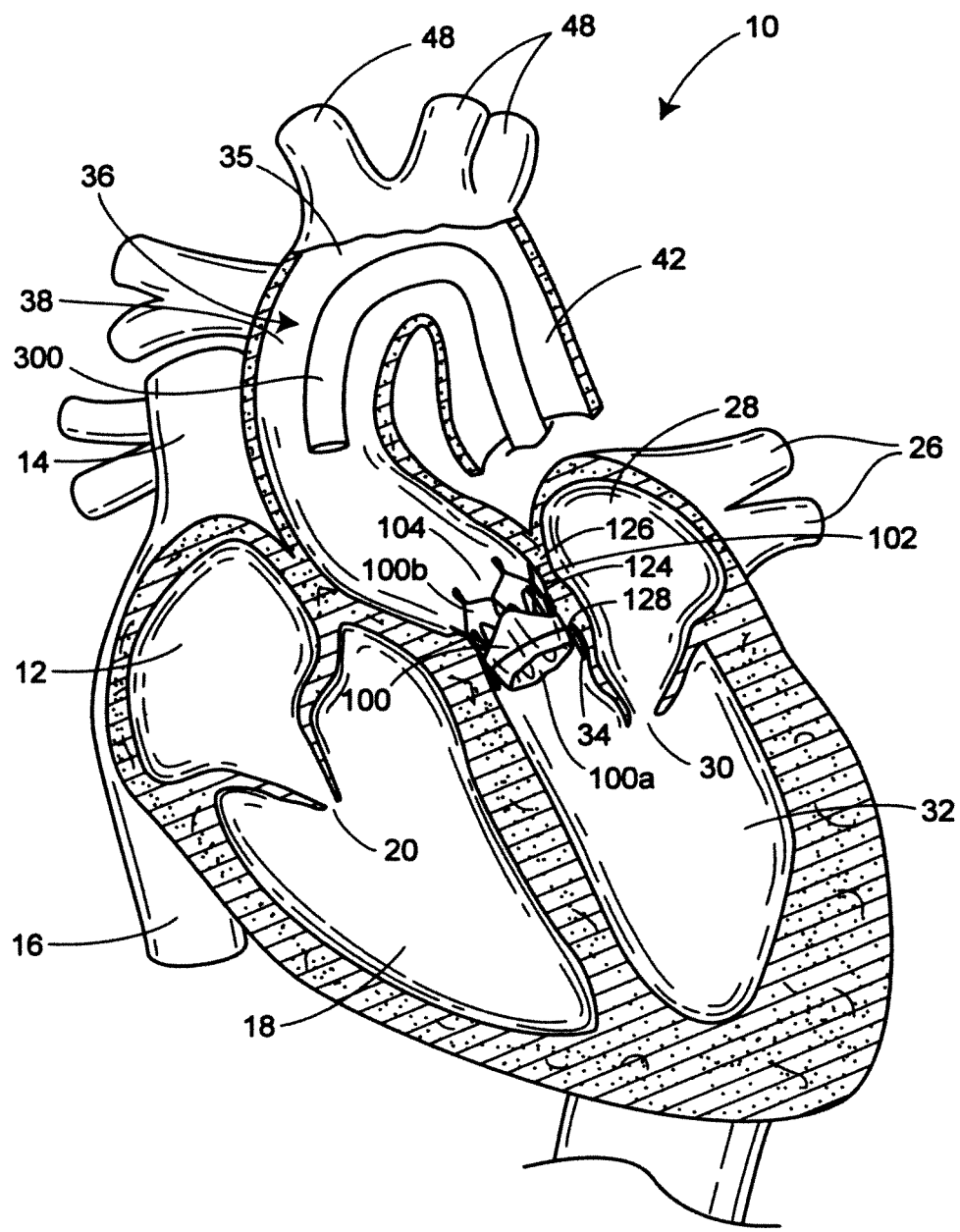
FIG. 2 is a cross-sectional representation of a heart including a collapsible heart valve prosthesis constructed in accordance with the teachings of the present disclosure.

FIG. 2 is a schematic illustration of the heart 10 implanted with a heart valve prosthesis 100, which is constructed in accordance with one embodiment of the present disclosure. In FIG. 2, the heart valve prosthesis 100 replaces the native aortic valve 34 and includes an inlet 100a and an outlet 100b. The outlet 100b is naturally located downstream from the inlet 100a along the flow of blood through the aorta 36. The heart valve prosthesis 100 will be described in detail below. Additionally, a means for and method of delivering the heart valve prosthesis 100 using an intravascular delivery system 300 (shown in FIG. 2) is described below.

While the following disclosure primarily focuses on replacing or repairing an abnormal or diseased aortic valve 34, the various features, aspects, structures, and methods disclosed herein are applicable to replacing or repairing the mitral 30, pulmonary 22, and/or tricuspid 20 valves of the heart 10 as those of ordinary skill in the art will appreciate. In addition, those of ordinary skill in the art will also recognize that the various features and aspects of the methods and structures disclosed herein can be used in other parts of the body that include valves or can benefit from the addition of a valve, such as, for example, the esophagus, stomach, ureter and/or vesice, biliary ducts, the lymphatic system and in the intestines.

Figure 3A:
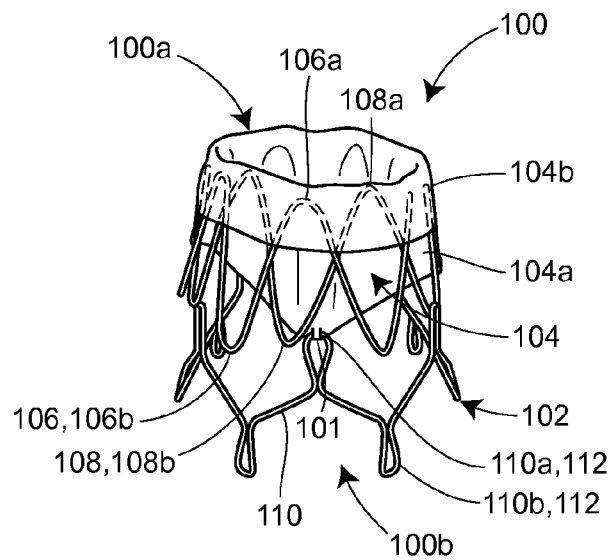
FIGS. 3A-3C are side, top, and bottom views, respectively, of a collapsible heart valve prosthesis constructed in accordance with the teachings of the present disclosure.
Figure 3B:
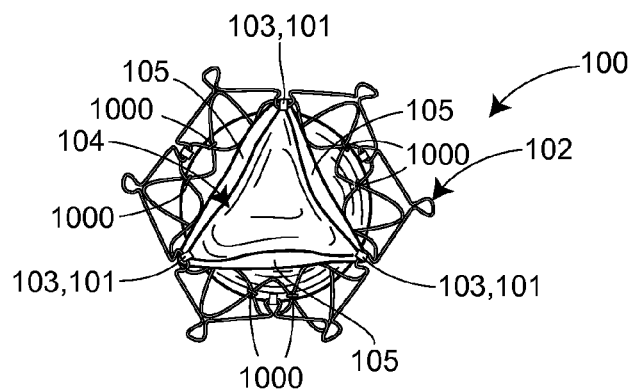
Figure 3C:
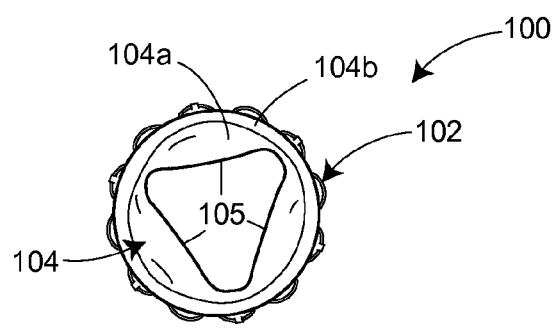

Referring now to FIGS. 3A-3C, one embodiment of the heart valve prosthesis 100 of the present disclosure will be described. In general, the heart valve prosthesis 100 includes a stent 102 and a multi-leaflet valve 104. The stent 102 is collapsible to facilitate intravascular delivery to the heart 10, with a catheter for example, as will be described below.

The multi-leaflet valve 104 includes a one-piece valve component, i.e., it is constructed from a single piece of material, positioned at the inlet 100a of the prosthesis 100. More specifically, the multi-leaflet valve 104 includes a single piece of material having a generally cylindrical valve portion 104a and a generally cylindrical cuff portion 104b. Because the multi-leaflet valve 104 is constructed from a single piece of material, the cuff portion 104b rolls outward and back upon or concentric with the valve portion 104a. As such, the valve portion 104a is disposed inside of the stent 102 and the cuff portion 104b is disposed outside of the stent 102. So configured, the cuff portion 104b serves to reduce or prevent regurgitation when the prosthesis is implanted in the heart 10, as depicted in FIG. 2. In the disclosed embodiment, the multi-leaflet valve 104 is secured to the stent 102 at a plurality of locations using conventional surgical sutures 101 (see, e.g., FIGS. 3A and 3B), but it should be appreciated that other devices for fixing the two components together are intended to be within the scope of the disclosure.

As shown in FIG. 3B, the valve portion 104a of the multi-leaflet valve 104 is secured to the stent 102 at three distinct points, each of which are identified with reference numeral 103. So secured, the valve portion 104a includes three walls 105 defined as being located between the points 103. Each of the walls 105 serves as one leaflet of the multi-leaflet valve 104, thereby defining the multi-leaflet valve 104 as a trileaflet valve. In other embodiments, the multi-leaflet valve 104 can include more or less than three leaflets, as desired.

In one embodiment, the multi-leaflet valve 104 is constructed of a polymer-coated polyester material. The polyester material can include Dacron™, which is commercially available from Bard Peripheral Vascular of Tempe, Ariz., USA, and the coating can include Quatromer™, which is commercially available from Innovia, LLC of Miami, Fla., USA.

In the disclosed form of the prosthesis, the stent 102 includes at least one length of wire bent and shaped such that the stent 102 has a multitude of turns forming a spring-like member that is resiliently deformable between an expanded state (shown in FIGS. 3A-3C) and a contracted state (not shown), wherein the stent 102 is collapsed upon itself in the radial direction. That is, in the contracted state, the prosthesis 100 has a radial dimension that is smaller than a radial dimension of the prosthesis 100 in the expanded state.

So configured, the stent 102 is biased toward the expanded state. When the prosthesis 100 is positioned in the heart 10, as depicted in FIG. 2, it occupies an active state that can be between the contracted state and the expanded state, for example, wherein the prosthesis 100 frictionally and forcefully engages the wall of the heart 10. This design therefore advantageously secures the position of the prosthesis 100 in the heart 10 without requiring any fasteners, mechanical or otherwise.

With continued reference to FIGS. 3A-3C, the stent 102 of the disclosed embodiment of the prosthesis 100 is formed such that the prosthesis occupies a generally tapered cylindrical shape. The stent 102 includes first through third lengths of wire, which are numbered 106, 108, and 110, respectively. Other embodiments can have less than or more than three lengths of wire. The first and second lengths of wire 106, 108 of the disclosed embodiment each occupy a wave pattern and are shaped into cylinders. In the present embodiment, the cylinders are generally tapered cylinders and the wave patterns constitute sinusoidal waves.

The second length of wire 108 is positioned radially inside of the first length of wire 106 and circumferentially offset therefrom. The first and second lengths of wire 106, 108 are secured together at a plurality of locations with conventional surgical sutures 1000 (see, e.g., FIG. 3B), but other devices for securing the two components together are intended to be within the scope of the disclosure. So configured, the sinusoidal patterns of the first and second lengths of wire 106, 108 can be described as being opposite in phase. That is, each peak 106a of the first length of wire 106 is aligned with each trough 108b of the second length of wire 108, and each peak 108a of the second length of wire 108 is aligned with each trough 106b of the first length of wire 106. For the sake of clarity, FIG. 3A only identifies one peak 106a, 108a and one trough 106b, 108b on each of the first and second lengths of wire 106, 108 with reference numerals. So configured, the first and second lengths of wire 106, 108 provide structural rigidity and integrity to the stent 102 and therefore, to the prosthesis 100.

The third length of wire 110 of the stent 102 of the prosthesis 100 depicted in FIGS. 3A-3C is also generally shaped as a tapered cylinder at least in the expanded state, and is attached to either or both of the first and second lengths of wire 106, 108 at a plurality of locations with conventional surgical sutures 1000 (see, e.g., FIG. 3B),. In other embodiments, the third length of wire 110 could be attached to the first and second lengths of wire 106, 108 with any other foreseeable device. In contrast to the sinusoidal patterns of the first and second lengths of wire 106, 108, however, the third length of wire 110 includes a wave pattern that also includes alternating bows. That is, the third length of wire 110 includes a plurality of peaks 110a and troughs 110b, but instead of the peaks 110a and troughs 110b having smooth sinusoidal transitions, each includes a bow 112. The bows 112 basically constitute small loops of wire extending away from the peaks 110a and troughs 110 b of the third length of wire 110. This design of the third length of wire 110 advantageously increases the radial stiffness of the stent 102, which increases the radial load generated by the prosthesis when it occupies the contracted and/or active states. Thus, it may be said that the third length of wire 110 is primarily responsible for generating the radial load required for securing the prosthesis in the heart 10, while the first and second lengths of wire 106, 108 are primarily responsible for maintaining the structural integrity of the overall prosthesis 100.

In one embodiment, the first, second, and third lengths of wire 106, 108, 110 each comprises a continuous piece of a shape memory nickel titanium alloy such as Nitinol. The wires 106, 108, 110 may be bound at the free ends with a length of stainless steel hypo-tubing and an adhesive, for example. In one form, the Nitinol wires are heat treated to retain the shapes and patterns illustrated in FIGS. 3A-3C. In other embodiments of the prosthesis 100, the wires 106, 108, 100 can be constructed of generally any other biocompatible material capable of serving the purpose of the stent 102.

Figure 4:
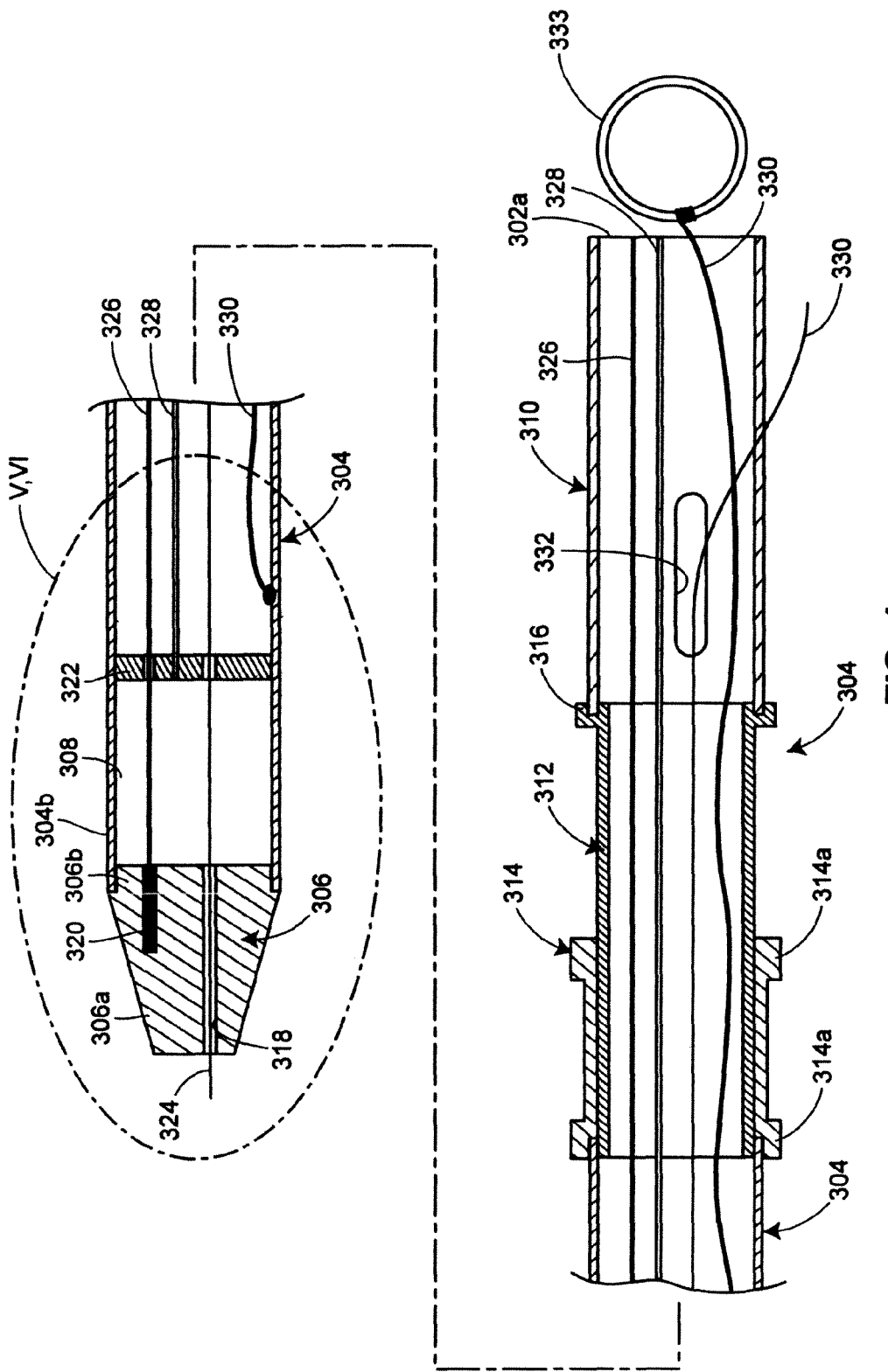
FIG. 4 is a cross-sectional side view of a system for intravascular delivery of a collapsible heart valve prosthesis constructed in accordance with the teachings of the present disclosure.

As mentioned above, the heart valve prosthesis 100 of the present disclose is designed to be implanted via intravascular delivery. One device for accomplishing such a delivery is depicted in FIGS. 4-6. Specifically, FIGS. 4-6 depict one embodiment of a system 300 for intravascular delivery of the heart valve prosthesis 100, which includes, for example, a catheter. The system 300 generally comprises a handle 302, an elongated flexible sheath 304, and a tip 306. In practice, the sheath 304 can be rather long, but for the sake of clarity, FIG. 4 illustrates the sheath 304 only at its end sections adjacent the handle 302 and the tip 306.

During use, the sheath 304 is adapted to store a heart valve prosthesis 100 in a cavity 308 formed adjacent to the tip 306. As such, the sheath 304 would preferably have an inner diameter of less than or equal to 7 millimeters and an outer diameter of less than or equal to 8 millimeters to sufficiently accommodate the large payload of the heart valve prosthesis 100, even when it is in its fully contracted state. So configured, the tip 306 and sheath 304 can be threaded through a blood vessel from a patient's groin, for example, to the heart 10 to deliver the prosthesis 100 in a manner that will be described below.

Referring to the bottom portion of FIG. 4, the handle 302 includes a hollow grip 310, a hollow slide rod 312, and a hollow spool 314. The grip 310 can be connected to the slide rod 312 at a threaded connection 316. The spool 314 is slidably mounted on the slide rod 312 and fixed to a first end 304a of the sheath 304 at a threaded connection 316. The spool 314 has a pair of radial flanges 314a for accommodating a user's grip, as will be described.

Referring now to the top portion of FIG. 4, the cavity 308 for receiving the heart valve prosthesis 100 is defined in a second end 304b of the sheath 304, which as mentioned is disposed adjacent the tip 306. The tip 306 includes a tapered body portion 306a and a plug portion 306b. The plug portion 306b is friction fit within the second end 304b of the sheath 304. The tip 306 further defines a through bore 318 and a blind bore 320 for receiving wires of the system 300, as will be described. Also, as depicted in FIG. 4, the second end 304b of the sheath 304 includes a stop plug 322 disposed therein. The stop plug 322 includes a generally solid cylindrical disk-shaped member having a plurality of bores therein for receiving various wires of the system, as will be described. The stop plug 322 defines the internal boundary of the cavity 308 for receiving the heart valve prosthesis 100.

As mentioned and illustrated in FIG. 4, the system 300 includes a plurality of wires extending through the sheath 304. Specifically, the system 300 includes a guide wire 324, a first stop wire 326, a second stop wire 328, and a maneuvering string 330.

The guide wire 324 passes through the through-bore 318 in the tip 306, through the sheath 304, through the handle 302, and out of an opening 332 formed in the grip 310 of the handle 302. The guide wire 324 is a conventional wire that a surgeon may first thread through the blood vessel to the heart 10 of the patient prior to threading the sheath 304 to the heart 10. When positioned in the blood vessel, the guide wire 324 guides the sheath 304 along the proper path to the heart 10.

The first stop wire 326 can be fixed to a back wall 302a of the handle 302, for example, and extends through the length of the handle 302 and sheath 304 and into the blind bore 320 of the tip 306. Accordingly, the first stop wire 326 also passes through an opening in the stop plug 322. The first stop wire 326 can be fixed to the stop plug 322 and the tip 306 with an adhesive, for example, to fix the position of the tip 306 and stop plug 322 relative to each other.

Similar to the first stop wire 326, the second stop wire 328 can be fixed to the back wall 302a of the handle 302, for example, and extends through the length of the handle 302 and sheath 304. Unlike the first stop wire 326, however, the second stop wire 328 stops at the stop plug 322. In one embodiment, the second stop wire 328 can be fixed into an opening or recess in the stop plug 322 with an adhesive, for example. In another embodiment, the second stop wire 328 may simply terminate immediately adjacent the stop plug 322. In either case, the second stop wire 328 serves to prevent the stop plug 322 from traveling up into the sheath 304 during operation, as will be described.

Finally, the maneuvering string 330 of the disclosed embodiment includes a first end that is fixed to a ring 333 adjacent the back wall 302a of the handle 302, and a second end that is fixed to the second end 304b of the sheath 304 at a location neat the stop plug 322, for example. The string 330 can include a conventional nylon string, a metallic wire, or generally any other type of material. While threading the sheath 304 into the patient's heart 10, a surgeon, for example, may pull the ring 333 to bend the second end 304b of the sheath 304 to help maneuver the sheath 304 through sharp turns. For example, with reference to FIGS. 1 and 2, this manipulation of the string 330 and sheath 304 may be beneficial to turn the second end 304b of the sheath 304 to traverse the aortic arch 35 when replacing the aortic valve 34.

Referring now to FIG. 5, as mentioned, the cavity 308 in the second end 304b of the sheath 304 is adapted to accommodate a heart valve prosthesis 100 in a contracted state, as depicted schematically in phantom. With the prosthesis 100 so loaded into the cavity 308, the tip 306 and sheath 304 can be threaded from the patient's groin, for example, and to the heart 10 such that the tip 306 is positioned just beyond the native aortic valve 34. Once the tip 306 is properly positioned, the surgeon, for example, grasps the spool 314 (shown in FIG. 4) of the handle 302 of the system 300 and pulls the spool 314 backwards along the slide rod 312 toward the grip 310. This movement of the spool 314 pulls the sheath 304 backwards such that the second end 304b of the sheath 304 disengages the plug portion 306b of the tip 306. The surgeon pulls the spool 314 until the second end 304b of the sheath 304 reaches the position depicted in FIG. 6.

With the sheath 304 out of the way, the heart valve prosthesis 100 is free to expand to an active state and engage the walls of the heart 10, as depicted in FIG. 2. During this process of setting the heart valve prosthesis 100, the first stop wire 326 maintains the position of the tip 306 relative to the stop plug 322 and the second stop wire 328 prevents the stop plug 322 from moving in the sheath 304 toward the handle 302. With the heart valve prosthesis 100 expanded and set in the heart 10, the surgeon can reengage the sheath 304 with the plug portion 306b of the tip 306 by pushing the spool 314 and sheath 304 away from the grip 310 of the handle 302. Then, the surgeon can draw the entire system back through the center opening of the prosthesis 100, out of the heart 10, and finally out of the patient's groin.

In view of the foregoing description, it should be understood that loading the heart valve prosthesis 100 into the cavity 308 of the sheath 304 can be accomplished by performing the above-described deployment steps in reverse. That is, with the heart valve prosthesis 100 in its expanded state, the tip 306 and second end 304b of the sheath 304 can be passed through the center thereof and the sheath 304 can be disengaged from the plug portion 306b of the tip 306 through manipulation of the spool 314 on the handle 302. With the prosthesis 100 and system 300 arranged as depicted in FIG. 6, a radial load can be applied to the circumference of the prosthesis 100. This radial load contracts the prosthesis 100 into a small cylinder that is able to fit into the cavity 308 of the sheath 304. The second end of the sheath 304 can then be slide over the prosthesis 100 either by manually grasping the second end 304b of the sheath 304 or through manipulation of the spool 314. Finally, the second end 304b of the sheath 304 can be friction fit onto the plug portion 306b of the tip 306. This completes the loading process.

Figure 7:
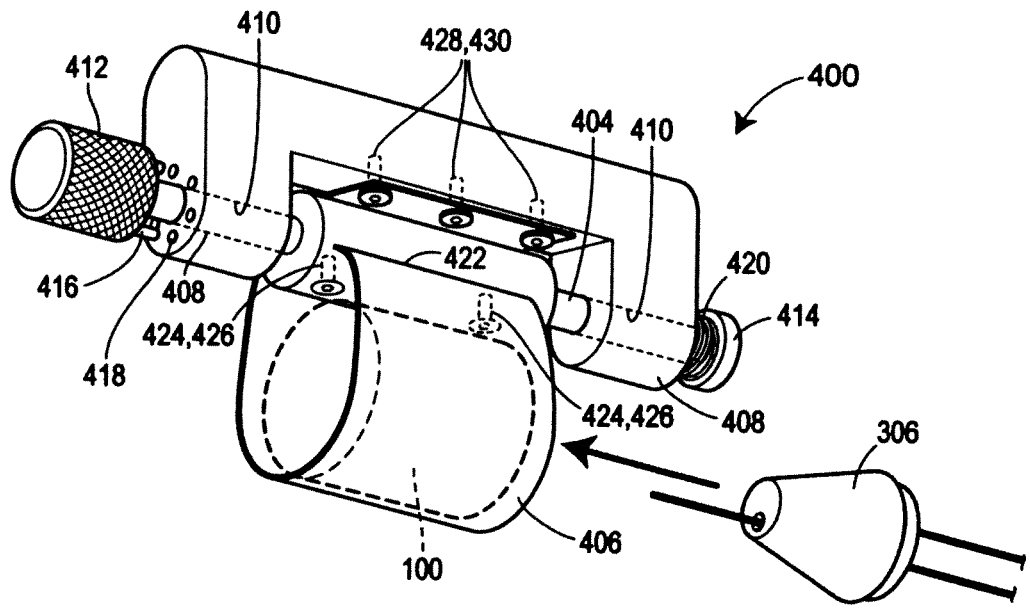
FIGS. 7 and 8 are side views of a device for loading the system of FIGS. 4-6 with a collapsible heart valve prosthesis constructed in accordance with the teachings of the present disclosure.
Figure 8:
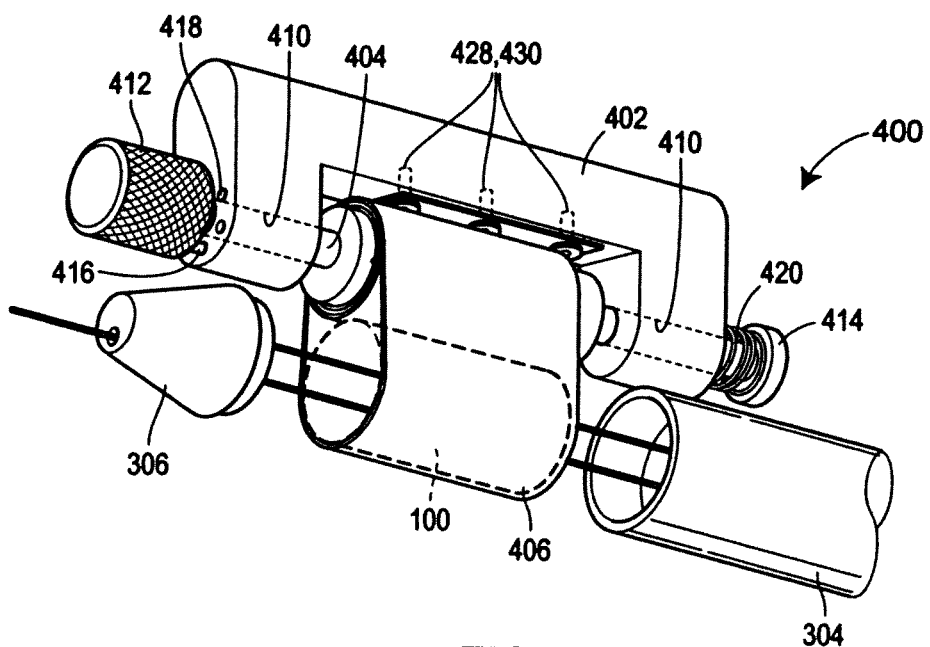

In one embodiment, the loading process can include the use of a device 400 for loading the heart valve prosthesis 100, such as that depicted in FIGS. 7 and 8. In the depicted embodiment, the device 400 includes a handle 402, a pin 404, and a loop of material 406. The handle 402 is a generally U-shaped member defining a pair of legs 408 having through-bores 410. Moreover, a plurality of threaded fasteners 428 are positioned in a corresponding plurality of threaded bores 430 formed in the handle 402.

The pin 404 is rotatably disposed in the through-bores 410 of the handle 402 and includes a knurled knob 412 on one end and a button 414 on the other end. The knurled knob 412 includes a pair of pins 416 adapted to be received in a pair of corresponding bores 418 formed in the handle 402 for locking rotation of the pin 404. The end of the pin 404 adjacent the button 414 accommodates a spring 420 between the button 414 and the adjacent leg 408 of the handle 402. Additionally, the pin 404 includes an elongated slot 422 formed in a central portion thereof and a pair of threaded fasteners 424 positioned in threaded bores 426 of the pin 404 that traverse radially to the elongated slot 422.

The loop of material 406 can include generally any type of material such as nylon, for example, and includes a first end 406a and a second end 406b. The first end 406a is fixed to the handle 402. More specifically, the first end 406a of the loop of material 406 includes a plurality of holes (not shown) that receive the plurality of fasteners 428 such that the fasteners 428 can be tightened against the handle 402 to fix the position of the first end 406a of the loop of material 406.

The second end 406b of the loop of material 406 is fixed to the pin 404. More specifically, the second end 406b of the loop of material 406 is received in the slot 422 formed in the pin 404 and the fasteners 424 are tightened to clamp the second end 406b of the loop of material 406 in place.

As depicted in FIG. 7, when the loop of material 406 is fixed to the device 400, it is adapted to receive the heart valve prosthesis 100 (shown schematically in phantom) in its expanded state. To contract the prosthesis 100, a user pulls knurled knob 412 of the pin 404 to the left relative to the orientation of FIG. 7. This pulls the pins 416 on the knurled knob 412 out of the corresponding bores 418 such that the user can rotate the pin 404. Rotation of the pin 404 rolls the loop of material 406 onto the pin 404 which thereby apples a radial force to collapse the heart valve prosthesis 100 from the expanded state to the contracted state, which is depicted schematically in phantom in FIG. 8. A radial dimension of the heart valve prosthesis 100 in the contracted state is less than a radial dimension of the heart valve prosthesis 100 in the expanded state such that the prosthesis 100 can be loaded into the cavity 308 of the sheath 304. Thus, with the prosthesis 100 sufficiently contracted, as depicted in FIG. 8, the surgeon or other user can manipulate the second end 304b of the sheath 304 into the loop of material 406 and around the prosthesis 100, and finally in engagement with the plug portion 306b of the tip 306. With the prosthesis 100 thus loaded, it can be implanted according to the process described above.

In light of the foregoing, it should be appreciated that the present disclosure provides a heart valve prosthesis 100 adapted for intravascular delivery and which is constructed completely of synthetic materials that are more resistant to degradation and rejection than animal based materials. Moreover, the prosthesis 100 advantageously retains its position in the heart 10 with friction and self-loading and does not require the use of any sutures, hooks, or other type of invasive mechanical fasteners.

Furthermore, the present disclosure advantageously provides a unique system for implanting a heart valve prosthesis. The system 300 disclosed with reference to FIGS. 4-6 advantageously enables the surgeon to remotely deflect the tip 406 of the system 300 in vivo through the use of the maneuvering string 300, thereby facilitating the traversal of difficult passageways such as the aortic arch. Additionally, the system 300 is advantageously designed to accommodate the large pay load of a heart valve prosthesis, which may have a diameter of approximately 25 millimeters in the fully expanded state and approximately 7 millimeters when occupying the contracted state within the sheath 304. Furthermore, the manual manipulation of the spool 314 relative to the grip 312 of the handle 310 provides for precise retraction of the sheath 304 and calculated deployment of the prosthesis 100.

The scope of the invention is not limited to the specific embodiments described hereinabove, but rather, is intended to be defined by the spirit and scope of the claims and all equivalents thereof.

The invention claimed is:

1. A heart valve prosthesis, comprising:
   a collapsible stent comprising a plurality of separate lengths of wire secured together with a plurality of sutures, each length of wire having a series of turns, wherein each length of wire is formed in the shape of a cylinder and axially overlaps with another length of wire of the plurality of lengths of wire such that a first length of the plurality of separate lengths of wire circumscribes a second length of the plurality of separate lengths of wire; and
   a one-piece multi-leaflet valve attached to the collapsible stent, the one-piece multi-leaflet valve comprising a cylinder of material secured to the collapsible stent at three points;
   wherein the stent is collapsible in a radial direction between a contracted state and an expanded state, the contracted state having a radial dimension smaller than a radial dimension of the expanded state, wherein the stent is spring biased toward the expanded state such that it occupies an active state when implanted into a heart, the active state having a radial dimension that is between the radial dimension of the contracted state and the radial dimension of the expanded state such that a radial load generated by the bias of the collapsible stent is sufficient to retain the heart valve prosthesis in the heart, wherein the series of turns in the plurality of separate lengths of wire define a plurality of alternating peaks, around which a cylindrical cuff of the one-piece multi-leaflet valve is wrapped, the cylindrical cuff for preventing regurgitation during use of the valve.

2. The heart valve prosthesis of claim 1, wherein, each of the first and second lengths of wire occupying a sinusoidal pattern.

3. The heart valve prosthesis of claim 2, wherein the first and second lengths of sinusoidal wires are disposed adjacent to each other and in opposite phase to provide structural integrity to the collapsible stent.

4. The heart valve prosthesis of claim 2, wherein the plurality of lengths of wire further comprises a third length of wire occupying a pattern of alternating bows and attached to the first and second lengths of wires at a location axially offset therefrom, the third length of wire serving to bias the collapsible stent into the expanded state.

5. The heart valve prosthesis of claim 1, further comprising surgical sutures connecting the one-piece multi-leaflet valve to the collapsible stent.

6. A heart valve prosthesis, comprising:
a collapsible stent comprising first and second lengths of wire, each of the first and second lengths of wire being a separate member occupying a wave pattern defining a plurality of alternating peaks and formed in the shape of a cylinder, the second length of wire positioned radially inside of the first length of wire and axially overlapping with the first length of wire such that the first length of wire circumscribes the second length of wire and, in combination, the first and second lengths of wire provide structural rigidity and integrity to the collapsible stent; and
a one-piece multi-leaflet valve attached to the collapsible stent, the one-piece multi-leaflet valve comprising a cylinder of material secured to the collapsible stent at three points and having a cylindrical cuff wrapped around the alternating peaks of the first and second lengths of wire, the cylindrical cuff for preventing regurgitation during use of the valve,
wherein the stent is collapsible in a radial direction between a contracted state and an expanded state, the contracted state having a radial dimension smaller than a radial dimension of the expanded state,
wherein the stent is spring biased toward the expanded state such that it occupies an active state when implanted into a heart, the active state having a radial dimension that is between the radial dimension of the contracted state and the radial dimension of the expanded state such that a radial load generated by the bias of the collapsible stent is sufficient to retain the heart valve prosthesis in the heart.

7. The heart valve prosthesis of claim 6, wherein the first and second lengths of wire occupy sinusoidal patterns defining the plurality of peaks and also defining a plurality of valleys, the sinusoidal patterns of the first and second lengths of wire being disposed approximately opposite in phase to each other to provide structural integrity to the collapsible stent.

8. The heart valve prosthesis of claim 7, wherein the collapsible stent further comprises a third length of wire occupying a pattern of alternating bows and attached to the first and second lengths of wires at a location axially offset therefrom.

9. The heart valve prosthesis of claim 6, wherein the first and second lengths of wire are secured together with a plurality of sutures.

10. The heart valve prosthesis of claim 6, further comprising surgical sutures connecting the one-piece multi-leaflet valve to the collapsible stent.

11. A heart valve prosthesis, comprising:
a collapsible stent comprising first, second, and third lengths of wire,
the first and second lengths of wire being separate members formed in the shape of cylinders and occupying sinusoidal patterns defining a plurality of peaks and valleys, the sinusoidal patterns of the first and second lengths of wire being disposed approximately opposite in phase to each other,
the second length of wire positioned radially inside of the first length of wire and axially overlapping with the first length of wire such that the first length of wire circumscribes the second length of wire,
the third length of wire being a separate member from the first and second lengths of wire and occupying a wave pattern of alternating peaks and troughs, each peak and each trough including a bow defined by a small loop of wire extending away from the corresponding peak or trough, the third length of wire attached to the first and second lengths of wires at a location axially offset therefrom; and
a one-piece multi-leaflet valve attached to the collapsible stent, the one-piece multi-leaflet valve comprising a cylinder of material secured to the collapsible stent and having a cylindrical cuff wrapped around the alternating peaks of the first and second lengths of wire, the cylindrical cuff for preventing regurgitation during use of the valve,
wherein the stent is collapsible in a radial direction between a contracted state and an expanded state, the contracted state having a radial dimension smaller than a radial dimension of the expanded state,
wherein the stent is spring biased toward the expanded state such that it occupies an active state when implanted into a heart, the active state having a radial dimension that is between the radial dimension of the contracted state and the radial dimension of the expanded state such that a radial load generated by the bias of the collapsible stent is sufficient to retain the heart valve prosthesis in the heart.

* * * * *